(12) United States Patent
Imada et al.

(10) Patent No.: US 6,805,859 B2
(45) Date of Patent: Oct. 19, 2004

(54) SYMBIOTIC FUNGUS (75) Inventors: Takahiro Imada, Fujinomiya (JP);
Naoya Hiruma, Fujinomiya (JP);
Yousuke Kurihara, Fujinomiya (JP);
Satoshi Shinozaki, Tokyo (JP); Miho Shimaike, Tokyo (JP); Junya Mizutani, Sapporo (JP)

(73) Assignee: Mayekawa Manufacturing Co., Ltd., Tokyo (JP)

( * ) Notice: Subject to any disclaimer, the term of this patent is extended or adjusted under 35 U.S.C. 154(b) by 69 days.

(21) Appl. No.: 09/824,590

(22) Filed: Apr. 3, 2001

(65) Prior Publication Data

US 2002/0040487 A1 Apr. 4, 2002

(30) Foreign Application Priority Data

Apr. 5, 2000 (JP) .......................................... 2000-103599

(51) Int. Cl.⁷ ............................................... A01N 63/00
(52) U.S. Cl. ..................... 424/93.5; 435/254.1; 504/117
(58) Field of Search ........................ 435/254.1; 504/117; 424/93.5

(56) References Cited

PUBLICATIONS

Bacon, et al., Can. J. Bot. (1981), 59(12), 2534–8.*
Bacon et al., J Gen Microbiol, (1979) 113 (1), 119–126.*
Porter, et al., J. Agric. Food Chem. (1981), 29(3), 653–7.*
Cagas, et al., Grass and Forage Science (1999), 54(4), 365–370.*

* cited by examiner

Primary Examiner—Irene Marx
(74) Attorney, Agent, or Firm—Kanesaka & Takeuchi (57) ABSTRACT A symbiotic fungus is a filamentous fungus of a biologically pure culture. The filamentous fungus belongs to genus Neotyphodium and a final metabolic product thereof is a chanoclavine. Plant with the filamentous fungus introduced therein has resistance to pest and do not show toxicity to livestock.

1 Claim, 10 Drawing Sheets

Lanes 1, 7, 14: Chanoclavine sample
Lanes 2, 3, 4, 5, 6, 8, 9, 10, 11, 12, 13: Extracts of plants infected with the endophytes deposited at the Japanese national Institute of Bioscience and Human Technology

Lanes 1, 10, 17: Chanoclavine sample
Lanes 2, 15: Extracts of plants infected with endophytes not deposited at the Japanese National Institute of Bioscience and Human Technology
Lanes 3, 16: Extracts of plants infected with endophytes not deposited at the Japanese National Institute of Bioscience and Human Technology + superimposed Samples
Lanes 4, 6, 8, 11, 13: Extracts of plants infected with the endophytes deposited at the Japanese National Institute of Bioscience and Human Technology
Lanes 5, 7, 9, 12, 14: Extracts of plants infected with endophytes not deposited at the Japanese National Institute of Bioscience and Human Technology + superimposed samples

+: Plants infected with the endophytes deposited at the Japanese National Institute of Bioscience and Human Technology
-: Plants infected with endophytes other than those deposited at the Japanese National Institute of Bioscience and Human Technology

FIG. 11

+: Plants infected with the endophytes deposited at the Japanese National Institute of Bioscience and Human Technology
-: Plants infected with endophytes other than those deposited at the Japanese National Institute of Bioscience and Human Technology

FIG. 12

SYMBIOTIC FUNGUS

BACKGROUND OF THE INVENTION

1. Field of the Invention

This invention relates to symbiotic fungi, plants into which a symbiotic fungus is artificially introduced, and a method of introducing a symbiotic fungus into plants. More particularly, this invention relates to a fungus, i.e., an endophyte, whose final metabolic product is chanoclavine, to a plant which can be used for pasture which such an endophyte is caused to infect, and to a method of infecting the plant.

2. Description of the Related Art

Japanese Patent Opening Heisei 5-317092 (Gazette), for example, discloses a method wherein a test is performed to discover whether or not an endophyte is living in plant tissue, e.g., callus derived from perennial rye grass, and after introducing an endophyte into callus which is confirmed not to contain endophyte, the endophyte is introduced to perennial rye grass wherein the plant tissue is reproduced.

A symbiotic fungus, i.e. an endophyte, is a filamentous fungus which lives in plant tissue, and it is know that the plants infected by such filamentous fungus have improved resistance to pests, resistance to disease, better growth rate, and resistance to environmental stresses such as heat and dryness, as compared with individuals which are not so infected. Thus, artificial infection with an endophyte leads to an improvement of plant characteristics.

Figure 1:
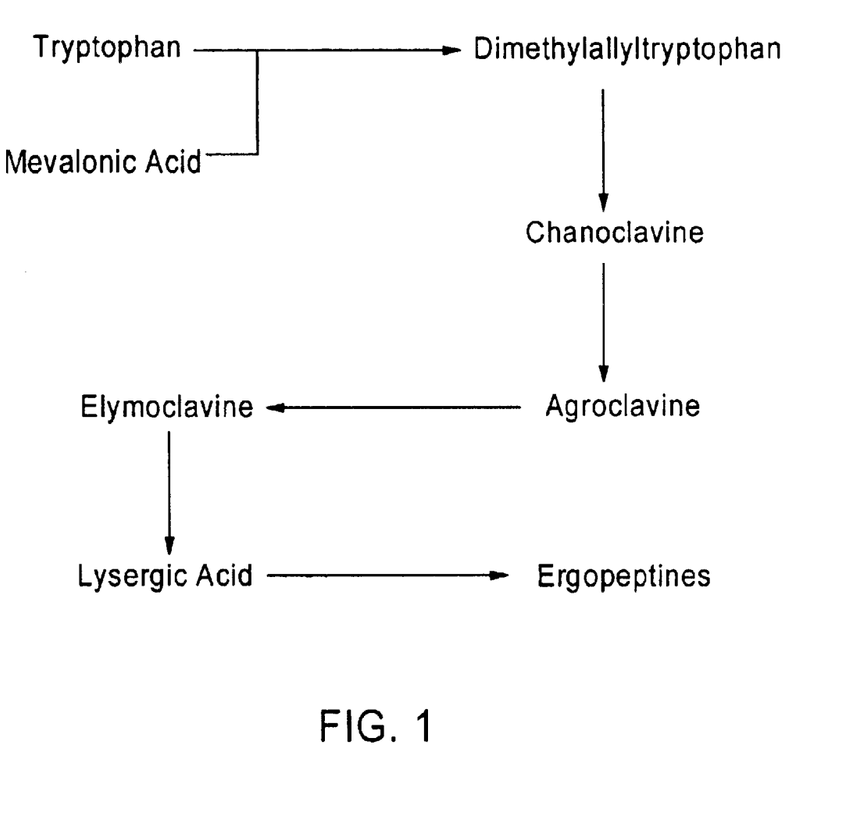
FIG. 1 is a flowchart showing the alkaloid metabolism of a symbiotic fungus.

Symbiotic fungi which can infect and live in plants successively biosynthesize the metabolic products shown in FIG. 1. The end product of this biosynthesis is an ergopeptine such as ergovaline or ergotamine.

It is known that grasses which are symbiotically infected by such endophytes show toxicity due to the presence of ergoto alkaloids. This toxicity is considered to be a problem in husbandry as it affects livestock. In the case of pasture, for example, grasses infected with endophytes such as perennial rye grass and tall fescue are very commonly distributed, and cases of poisoning have been reported due to ergoto alkaloids.

Rye grass slugger was first reported by New Zealand in 1906, and occurs mainly in two countries in Oceania, i.e., New Zealand and Australia. Rye grass slugger occurs when endophytes infect perennial rye grass which has withered in the severity of the dry conditions from summer to autumn, and livestock such as sheep eat the grass.

In rye grass slugger, livestock which ate grass show various symptoms. i.e, their limbs stiffen, and the neck, shoulder and flank shake. In other words, a kind of spasm occurs, and if this state continues, the animals become weaker. In the worst case, they are no longer able to move and may starve to death. It has now become clear that the substance responsible for this is Lolitrum B, which is a Lolitrum alkaloid.

Fescue toxicosis mainly occurred in the American southeast. Cows which consumed tall fescue suffered serious weight loss, and did not eat sufficient fodder. Their milk production declined, and their birth rate also fell. Endophytes were found to have infected the grass which the cows had eaten, and ergovaline which is an ergoto alkaloid was specifically detected from endophyte-infected plant individuals. It thus became clear that ergovaline causes fescue toxicosis.

Although resistance to pests, resistance to disease, growth rate and resistance to environmental factors such as heat and dryness are improved by infecting plants, especially pastures, with an endophyte, the endophytes biosynthesized substances which are poisonous to livestock, and gave rise to the problem of rye grass slugger, fescue toxicosis, etc.

OBJECTS AND SUMMARY OF THE INVENTION

It is therefore an object of this invention to solve the above problem.

It is an another object of this invention to provide a symbiotic fungus which improves plant characteristics without synthesizing poisonous substances when applied to grass.

A further object of this invention is to provide plants into which said symbiotic fungus is artificially introduced, and to provide a method of artificially introducing the symbiotic fungus.

A still further object of this invention is to provide a plant not showing livestock toxicity and having strong resistance to pest.

According to one aspect of this invention, there is provided a symbiotic fungus comprising a filamentous fungus whose final metabolic product is chanoclavine. The symbiotic fungus meant here may belong to the genus Neotyphodium. The symbiotic fungus may also be one, two or more types of fungi deposited at the Japanese National Institute of Bioscience and Human Technology under the numbers FERM P-17672 (BP-08480), FERM P-17673 (BP-08481) and FERM P-17674 (BP-08482).

The invention relating to a symbiotic fungus whose final metabolic product is chanoclavine, is selected by screening for using chanoclavine as a marker. Here, the screening may be performed using thin layer chromatography or liquid chromatography using chanoclavine as a marker.

The invention relating to a plant, concerns a plant into which the symbiotic fungus whose final metabolic product is chanoclavine, is introduced. Here, the symbiotic fungus may be a filamentous fungus belonging to the genus Neotyphodium. The plant into which the symbiotic fungus is artificially introduced may be a grass which is any of Agrostis, Festuca, Poa and Lolium. Later generations of seeds taken from these plants, plants grown from later generations of seeds, or hybrid plants having these plants and seeds as parents, are also within the scope of this invention.

One invention relating to a method of introducing a symbiotic fungus, comprises a step for isolating symbiotic fungi from plants which exist naturally, a step for artificially cultivating the isolated symbiotic fungi, a step for introducing the cultivated symbiotic fungi into target plants, a step for infecting the plants with the introduced symbiotic fungi, and a step for selecting a plant infected with a symbiotic fungus whose final metabolic product is chanoclavine.

Another invention relating to a method of introducing a symbiotic fungus, comprises a step for isolating symbiotic fungi from plants which exist naturally, a step for artificially cultivating the isolated symbiotic fungi, a step for selecting a symbiotic fungus whose final metabolic product is chanoclavine from the cultivated symbiotic fungi, a step for introducing the selected symbiotic fungus into a target plant, and a step for infecting the plant with the introduced symbiotic fungus.

The alkaloid metabolism of the symbiotic fungus is shown in FIG. 1. Chanoclavine is an intermediate product of such metabolism. Chanoclavine is a clavine alkaloid having the chemical structure shown in FIG. 2, and it has various pharmacological effects. Ergotoalkaloids such as ergovaline are produced from chanoclavine. However, in the symbiotic fungi searched by the Inventor, the ergotoalkaloids were not biosynthesized and chanoclavine was produced as the final metabolic product. The symbiotic fungus whose final metabolic product is chanoclavine does not show ergovaline toxicity. Therefore, plants which do not show ergovaline toxicity can now be provided by making such a symbiotic fungus infect the plant.

The present Application, which specifically concerns a symbiotic fungus which biosynthesizes chanoclavine as its final metabolic product, involves screening before and after introduction of the fungus into the plant, followed by infection of the plant with the fungus. Filamentous fungi belonging to the genus Neotyphodium are examples of symbiotic fungi which infect grasses.

Using this type of filamentous fungi, filamentous fungi which biosynthesize chanoclavine as their final metabolic product infect the plants. Hence plants can be produced which, although they do not show ergovaline toxicity, still have improved characteristics. Also, as plants infected with filamentous fungi which biosynthesize chanoclavine as a final metabolic product, accumulate large amounts of chanoclavine in their tissues, it is possible to provide a fungus which does not biosynthesize ergovaline or Lolitrum B by screening using chanoclavine as a marker.

This invention relates to a symbiotic fungus comprising a filamentous fungus, to a filamentous fungus having chanoclavine as its final metabolic product, to plants into which this type of symbiotic fungus is artificially introduced, and to a method of introducing the symbiotic fungus into plants.

According to this invention, therefore, plants which have been artificially infected with this symbiotic fungus do not biosynthesize toxic substances such as ergotoalkaloids like ergovaline and Lolium B, and do not present any toxicity risks to livestock when used as pasture grass. Therefore, rye grass slugger and fescue toxicosis can be prevented beforehand. Moreover, the plants thus produced show a strong resistance to pests due to the endophyte with which they are infected. Accordingly it is possible to provide the plants having excellent pest resistance and have no toxicity to livestock.

The above and other objects, features and advantages of the invention will be apparent from the following description of illustrative embodiments and examples, which are to be read in connection with accompanying drawings.

DETAILED DESCRIPTION OF THE PREFERRED EMBODIMENTS

A first embodiment of this invention allows the provision of plant individuals infected with an endophyte which specifically biosynthesizes chanoclavine, and screening for endophytes which do not biosynthesize ergotoalkaloids and Lolitrum B using chanoclavine as a marker. This embodiment will be described according to the procedure below.

Stage 1 Detection and Isolation of Endophyte (1) Detection of Endophyte

The epidermis of the leaves and sheaths of plants collected in a search were peeled and stained by immersing in analine blue staining solution, any endophyte in the tissue was detected under an optical microscope, and the presence or absence of endophyte thus confirmed.

(2) Isolation and Bioculture of Endophyte

Explants in which endophyte was confirmed were sterilized, transplanted to an endophyte isolation bioculture and cultured for several months.

(3) Classification of Endophytes

The isolated endophyte was classified according to host. Alternatively, bioculture was performed under different environmental conditions using the flat plate culture method, and a classification made according to morphological characteristics; or a liquid culture was performed and a classification made according to morphological characteristics; or a slide culture was performed and a classification made according to morphological characteristics.

Stage 2 Introduction of Endophyte

The isolated endophyte was artificially introduced into plants in any of the genuses Agrostosis, Festuca, Lolium and Poa which are target grasses. The endophyte was introduced by direct inoculation of the plant, or by preparing undifferentiated cells such as callus from the plant and inoculating, and regenerating the plant from callus. These methods may be chosen arbitrarily according to the type of plant in which the endophyte is to be introduced.

Stage 3 Confirmation of Endophyte Introduction

Explants taken from individuals into which the endophyte was introduced were stained by a staining solution, observed under an optical microscope, and the endophyte, or presence or absence of infection, was detected using the enzyme immunoassay technique.

Stage 4 Examination of Plants Into which the Endophyte was Introduced (1) Detection of Chanoclavine Alkaloids which were biosynthesized in plants infected with the endophyte were analysed, and detection of chanoclavin, ergotoalkaloids and Lolitrum B was performed.

(2) Identification of Chanoclavine

An identification of whether or not the final metabolic product was chanoclavine, was made by determining whether or not the alkaloid which had been specifically biosynthesized and had collected in large amounts in plants infected with the endophyte, was chanoclavine.

(3) Pest Resistance Test

Pests considered to be harmful were bred, and a pest damage experiment was conducted artificially using plants infected with the endophyte.

(4) Tests Using Later Generations

Seeds in which endophyte was present were collected and germinated, the presence of the endophyte was confirmed, and the above tests were then performed.

Stage 5 Biosynthesis of Chanoclavine on an Artificial Endophyte Bioculture Medium (1) Bioculture of Endophyte The isolated endophyte was biocultured under different environmental conditions using the flat plate culture method, and alkaloids were biosynthesized.

(2) Detection of Chanoclavine from Bioculture

Alkaloids biosynthesized from a bioculture in which the fungi had been cultured alone were analysed, and chanoclavine, ergotoalkaloids and Lolitrum B were detected.

Stage 6 Screening for Endophyte Using Chanoclavine as a Marker

Using the fungi, or plants infected with the fungi, endophytes were screened concerning their ability to biosynthesize chanoclavine alone without biosynthesizing ergotoalkaloids or Lolitrum B.

Next, another embodiment of this invention will be described. In the aforesaid embodiments in Stage 1–Stage 6, an identification was performed as to whether or not the infecting symbiotic fungus was a fungus which biosynthesizes chanoclavine as a final metabolic product by analysing the alkaloids which were biosynthesized in plants infected with the endophyte. Here however, instead of this step, the aforesaid identification was performed before artificially introducing the symbiotic fungus into the plant.

Specifically, in this embodiment, after culturing the endophyte isolated from plants collected in a search, the alkaloids in the endophyte were analysed, and an identification was performed as to whether or not the symbiotic fungi were producing chanoclavine as the final metabolic product. In other words, the difference from the aforesaid first embodiment is that the identification of chanoclavine is performed before introduction into the plant. The remaining features of the procedure are identical to those of the aforesaid first embodiment.

EXAMPLES

Example 1

(1) Analysis of Fungi

To isolate the endophyte from the plant, the leaf and leaf sheath were washed with water, immersed in a 70% aqueous solution of ethanol for 10 seconds, immersed in a 2.5% aqueous solution of sodium hypochlorite for 10 minutes, washed three times with sterile water, transferred to an endophyte isolation culture, and cultured in the dark at 25° C.

The isolation culture was prepared by sterilizing PDA (potato dextrose agar) adjusted to pH 5.6 at 121° C. for 15 minutes, adding 100 mg/l each of penicillin and streptomycin, and pipetting 20 ml portions into plastic Petri dishes of diameter 9 cm.

(2) Classification and Identification of Endophytes by Using the Flat Plate Culture Method The mycelium transplanted to the PDA culture was grown in the dark at 25° C., and the colonies formed were examined. On examination, the surfaces of the colonies on the culture were all white filaments, and their underside was also white. Their growth was relatively slow, and they grew to a radius of only about 3 cm in one month. On the corn meal agar culture, growth was much slower than on the PDA culture, the colonies growing to a radius of only about 1 cm in one month. The characteristics of the colonies were essentially identical to those of the PDA culture.

The isolated endophytes were deposited on Dec. 7, 1999 and accepted at the Japanese National Institute of Bioscience and Human Technology, which belongs to the Agency of Industrial Science and Technology. The description and deposition numbers of these endophytes are as follows.

FERN P-17672 (Neotyphodium sp. Po-060B)
FERN P-17673 (Neotyphodium sp. Po-062)
FERN P-17674 (Neotyphodium sp. Po-120)

(3) State of Mycelium by Slide Culture

A PDA culture of thickness 2–3 mm was mounted on a glass slide, mycelium was grown on the culture, and the morphology of the mycelium and formation of conidiospores was examined. This culture was performed at 25° C. in the dark.

On examination, it was found that all the mycelia were colorless, partitions of width 1–2 um being observed throughout. All the isolated endophytes were able to form conidiospores. The conidiospores were formed at the ends of single phialides emerging from the ends or sides of the mycelium, and most were single conidiospores.

All conidiospores were colorless, and monocellular. Most conidiospores were kidney-shaped and were 3–8×1–3 um in size. The phialides formed were all cylindrical tapering towards the ends, and isolated from the mycelium by partitions.

(4) Method of Introducing the Endophyte

For the inoculation, seeds were sterilized and sown on a WA culture (water Agar culture) comprising 0.8% agar added to water, and cultured under dark conditions. 3–7 days after starting the culture, a notch was inserted in the growth point of the plant with a knife, and mycelia cultured on the PDA medium were inserted.

After 8 days in the dark at 25° C. and 30° C. the plants were placed under illumination at 15° C. for 16 hours for 4 days, and placed under illumination at 25° C. for 16 hours for at least 2 days. Plants which had turned green were acclimatized in pots.

The epidermis of leaves and leaf sheaths of these plants were removed, and the presence or absence of endophyte in the tissue was confirmed by an optical microscope examination. This confirmation was performed as follows. 5 ml of lactic acid, 10 ml of glycerine, 5 ml of water and several drops of a staining solution comprising 0.02 g of an aqueous solution of aniline blue were placed on a glass slide. The leaf sheath was peeled away, and the underside epidermis was peeled away toward the leaf vein. The peeled epidermis was placed on the glass slide, covered with a cover glass, boiled in the flame of a gas burner, and the tissue was observed with an optical microscope. Under these conditions, if the endophyte is present, the mycelium appears blue, so the endophyte can be detected by this procedure.

As a result, the endophyte was detected in plants of the genuses Agrostis, Festuca, Poa and Lolium, which are grasses. From the life cycle of the fungus, this endophyte was found to be a Neotyphodium endophyte which reproduces only asexually and does not leave the plant.

It was also clear that FERM P-17672, FERM P-17673 and FERM P-17674, which were deposited at the Japanese National Institute of Bioscience and Human Technology, infected plants belonging to the genuses Agrostis, Festuca, Poa and Lolium, which are grasses.

(5) Artificial Inoculation Using Callus

Callus was induced in Agrostis, Festuca, Poa and Lolium, which are grasses, as specimens for artificial inoculation. A callus induction culture of these plants was prepared by adding 2.0 mg/l of 2,4-D(2,4-dichlorophenoxyacetic acid) and 0.2 mg/l of BAP (6-benzylaminopurine) to an MS base culture.

Seedlings obtained immediately after germination on an MS culture were transplanted to the callus induction cultures, and cultured for 2 months in the dark at 25° C. so as to obtain callus which had differentiating ability. All calluses were induced on the aforesaid induction culture, and then transferred to the MS base culture without addition of plant hormone.

These plant calluses were artificially inoculated with fungus of FERM P-17672, FERM P-17673 and FERM P-17674 deposited at the Japanese National Institute of Bioscience and Human Technology. Artificial inoculation was performed by taking a small amount of mycelium on the end of a knife, and transplanting it to the center of the callus.

The callus was cultured for several weeks in the dark at 25° C. and 30° C., then placed under illumination for 16 hours, or alternatively it was placed under illumination for 16 hours from the start. The regenerated plant was then transferred to a fresh MS culture and grown for one month. When an examination was made for presence of the endophyte according to the method described in (1), it was confirmed that the endophyte had been introduced.

(6) Method of Screening for Fungus which Specifically Synthesizes Chanoclavine in the Plant The leaves and leaf sheaths of plants artificially infected with FERM P-17672, FERM P-17673 and FERM P-17674 which were deposited at the Japanese National Institute of Bioscience and Human Technology and plants infected with other fungi which had been freeze-dried, were agitated and extracted for one day and night at room temperature by a chloroform/methanol/25% ammonia water=75/25/0.5 solution, filtered on filter paper, and evaporated. The presence of chanoclavine was confirmed by performing a TLC (Thin Layer Chromatography) analysis.

Figure 4A:
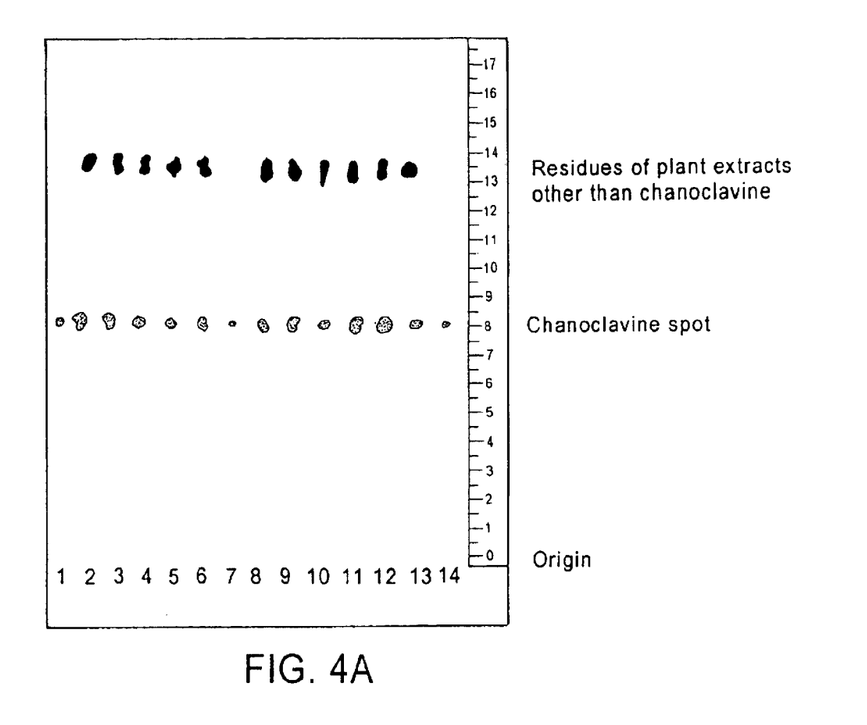
FIG. 4 shows photographs and an analysis chart of thin layer chromatography data.
Figure 4B:
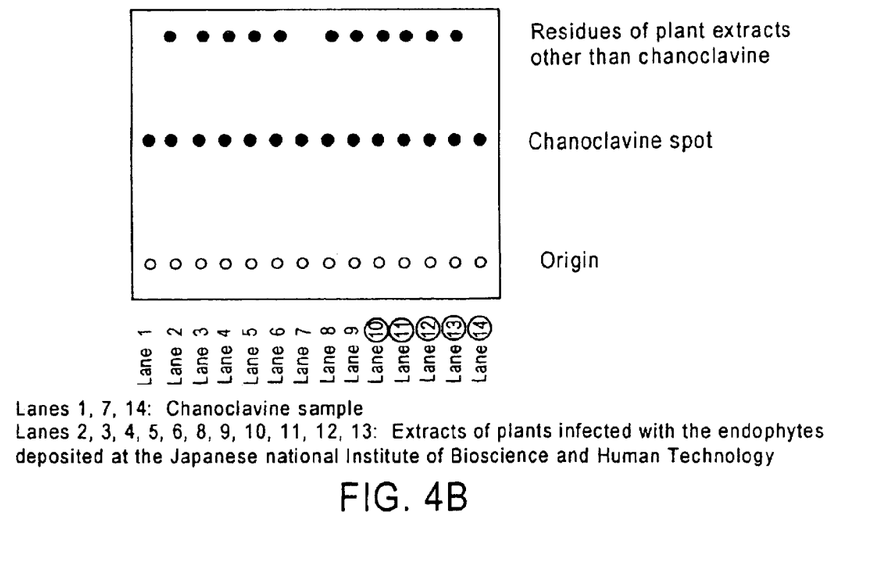

After developing on a silica gel 60 plate using chloroform/methanol/acidic acid/water=20/10/1/1 as developing solution, a spot detected by UV and the Eherlich reagent (bluish purple coloration) having an Rf value in the vicinity of 0.5–0.6 was found by TLC analysis as shown in FIG. 4. This spot had an identical Rf value to that of chanoclavine, and a spot having an identical Rf value was also found by a TLC analysis wherein an endophyte-infected plant extract was super-imposed on chanoclavine, as shown in FIG. 5.

Figure 5A:
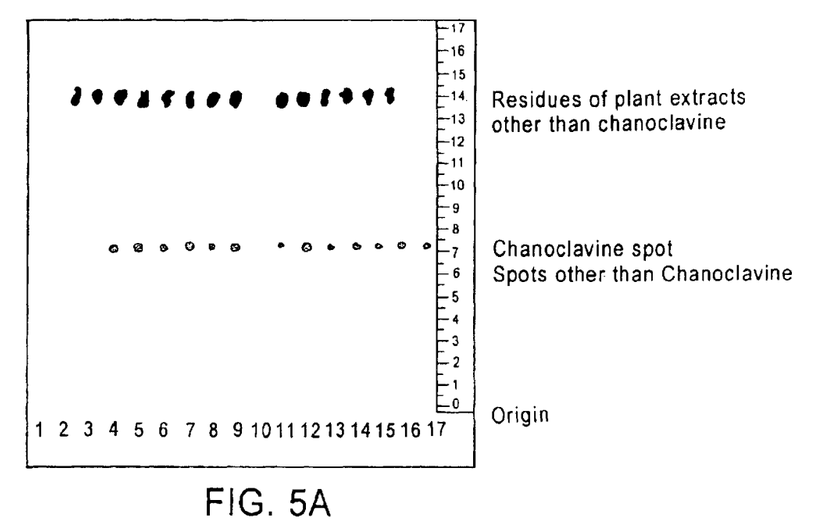
FIG. 5 shows photographs and an analysis chart of thin layer chromatography data.
Figure 5B:
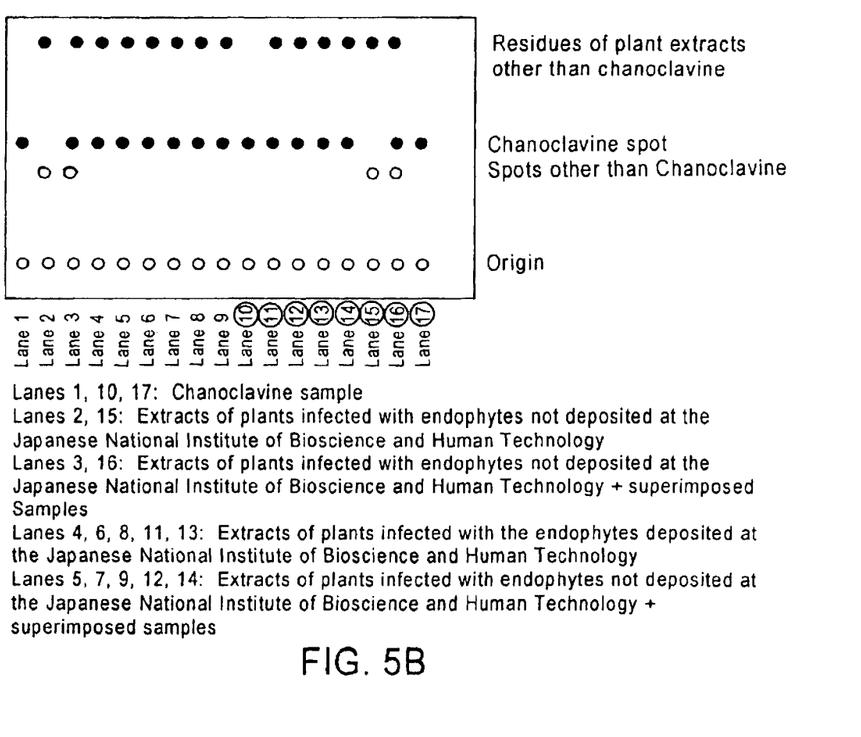

However, as seen in lane 2 and lane 15 in FIG. 5, a spot due to chanoclavine was not found in plants infected with endophytes other than the above fungi deposited at the Japanese National Institute of Bioscience and Human Technology. When chanoclavine was superimposed on the extracts of lane 2 and lane 15 as shown by lane 3 and lane 16 in this figure, a spot due to chanoclavine was then found as in the case of the lanes where chanoclavine was detected.

From the above results, it is clear that chanoclavine is biosynthesized and accumulates in plants infected specifically with the symbiotic fungi which were deposited at the Japanese National Institute of Bioscience and Human Technology, including Neotyphodium sp. FERM P-17672. Also, it was confirmed that the fungi infecting the plants could be screened for using the biosynthesis and accumulation of chanoclavine as a marker.

For plants which had been cultivated from later generations of seeds of plants infected with the fungi deposited at the Japanese National Institute of Bioscience and Human Technology, including Neotyphodium sp. FERM P-17672, the presence or absence of chanoclavine was also confirmed by TLC analysis. It was found that even in later generations of plants, biosynthesis of chanoclavine proceeded as in the case of the original plants.

(7) Method of Screening for Fungi which Specifically Synthesize Chanoclavine on Artificial Culture Endophytes, e.g., Neotyphodium sp. FERM P-17672, were isolated from plants synthesizing chanoclavine in endophyte-infected plants. To isolate the endophyte, the leaf and leaf sheath were washed with water, immersed in a 70% aqueous solution of ethanol for 10 seconds, immersed in a 2.5% aqueous solution of sodium hypochlorite for 10 minutes, washed three times with sterile water, cut to a a size of 5×5 mm, transferred to an endophyte isolation culture, and cultured in the dark at 25° C.

The isolation culture was prepared by adding 100 mg/l each of penicillin and streptomycin to PDA (potato dextrose agar), and pipetting 20 ml portions into plastic Petri dishes of diameter 9 cm.

At 3–8 weeks after starting the bioculture, the mycelium was isolated from plant tissue, and biocultured on a liquid culture medium. The biomedium was for example a PD (potato dextrose) medium, a M102 medium or an SM medium which is known to be an ergotoalkaloid-producing medium. 5×5 mm clumps of mycelia isolated on the PDA medium were introduced into 100 ml of the above biomedia, and cultured for from 2 weeks to as long as 6 months.

To confirm biosynthesis of chanoclavine, the biocultures were freeze-dried as in the case of the plants, introduced into a chloroform/methanol/25% ammonia water=75/25/0.5 solution, agitated and stirred for one day and night at room temperature, filtered on filter paper, and evaporated. TLC was then performed.

After developing on a silica gel 60 plate using chloroform/methanol/acidic acid/water=20/10/1/1 as developing solution, a spot detected by UV and the Eherlich reagent (bluish purple coloration) having an Rf value in the vicinity of 0.5–0.6 was found by TLC analysis as in the above case, showing that chanoclavine was being biosynthesized.

(8) Identification of Chanoclavine

Freeze-dried endophyte-infected plants, for example plants infected with FERM P-17672, FERM P-17673 and FERM P-17674 which were deposited at the Japanese National Institute of Bioscience and Human Technology, and the leaves and leaf sheaths of uninfected individuals, were extracted by shaking for at least 30 minutes at room temperature with an 80% aqueous solution of methanol. The extract was filtered on filter paper, the filtrate supplied to a VARIAN BOND ELUT CBA column packed with a negative ion exchange resin (AG2×8 200–400 mesh) suspended in an 80% aqueous solution of methanol substituted by 25% ammonia water, and rinsed with pure water. The filtrate was solved by a 5% formic acid solution, and the fractions obtained was provided for the analyses by TLC (Thin Layer Chromatography) and HPLC (High Performance Liquid Chromatography).

Figure 6:
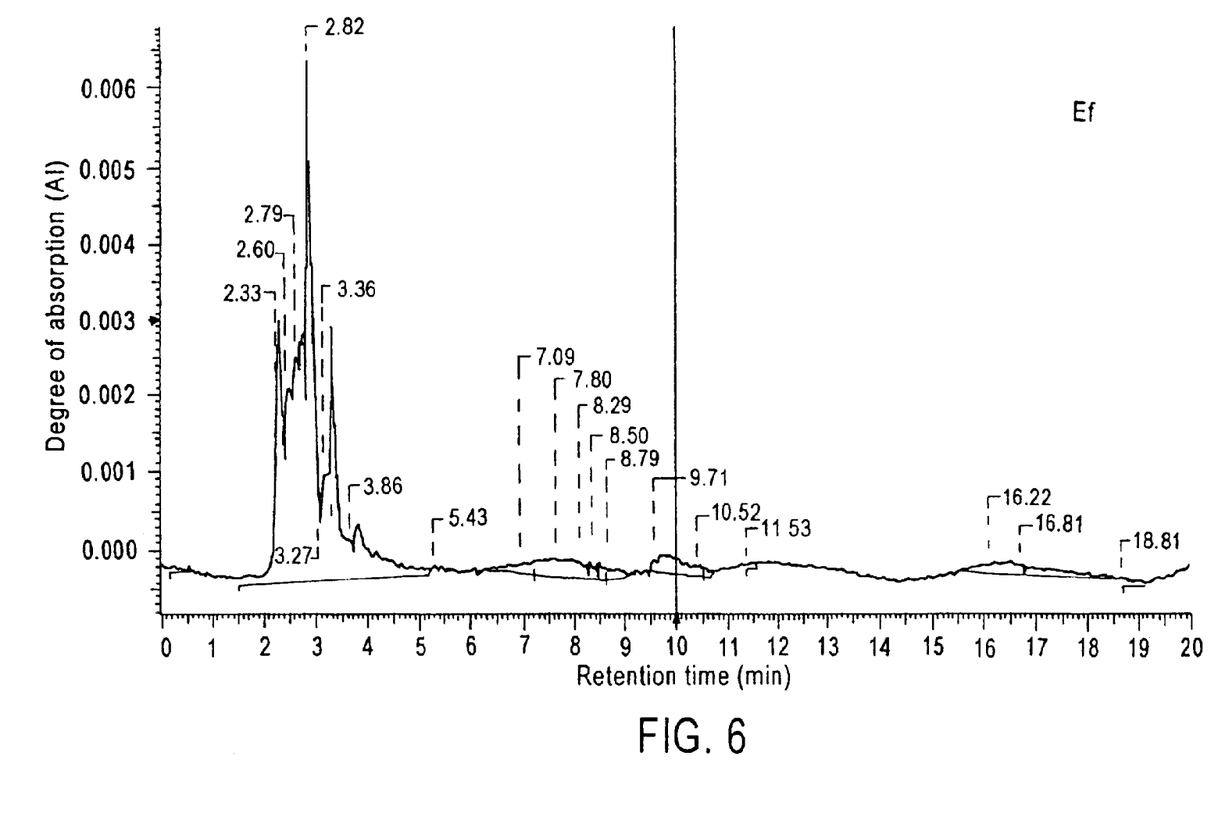
FIG. 6 is a graph showing the results of high performance liquid chromatography.
Figure 7:
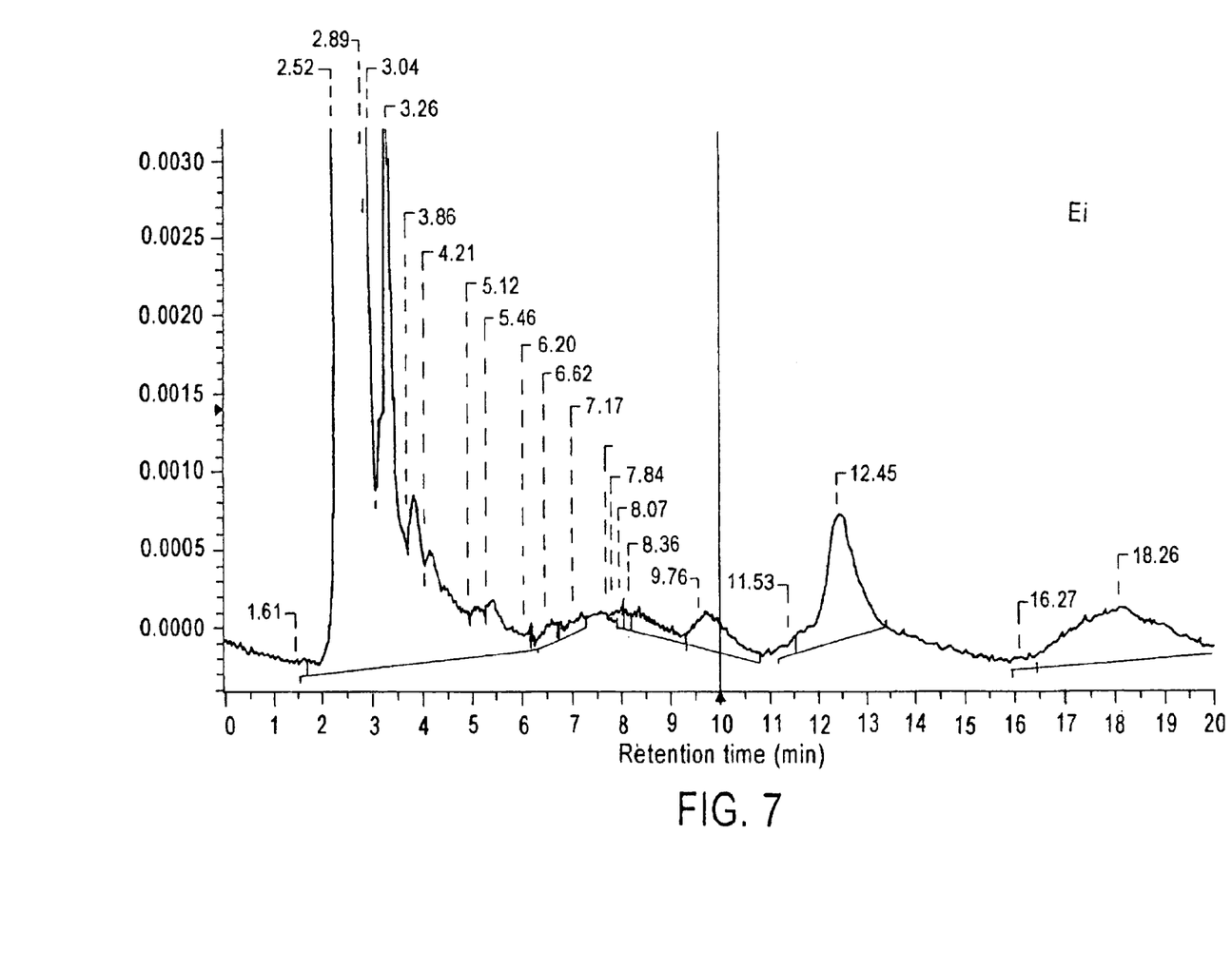
FIG. 7 is a graph showing the results of high performance liquid chromatography.

When the fraction obtained was analysed by HPLC using a C18 column (5 um particle size, 100×8 mm) and UV at 280 nm, a specific significant peak was obtained in the vicinity of a retention time in the vicinity of 12 minutes as shown in FIG. 7 only for the fractions obtained from the endophyte-infected plants. In the case of plants not infected by the endophytes, this peak was not found, as shown in FIG. 6.

After developing using a silica gel 60 plate and a developing solution of chloroform/methanol/acetic acid/water=20/10/1/1, a spot detected by UV and the Eherlich reagent (bluish purple coloration) having an Rf value in the vicinity of 0.5–0.6 was found by TLC analysis. The spot found by TLC was also specific for endophyte-infected plants, and was not observed for uninfected individuals.

This fraction was isolated by HPTLC. As a result, the recovery rate was 0.06–0.08% on average from freeze-dried samples. This fraction was also tested positive in fluorescent light detection by HPLC, suggesting an indole structure. Hence, the NMR, MS and IR (infrared analysis) were measured.

Figure 2:
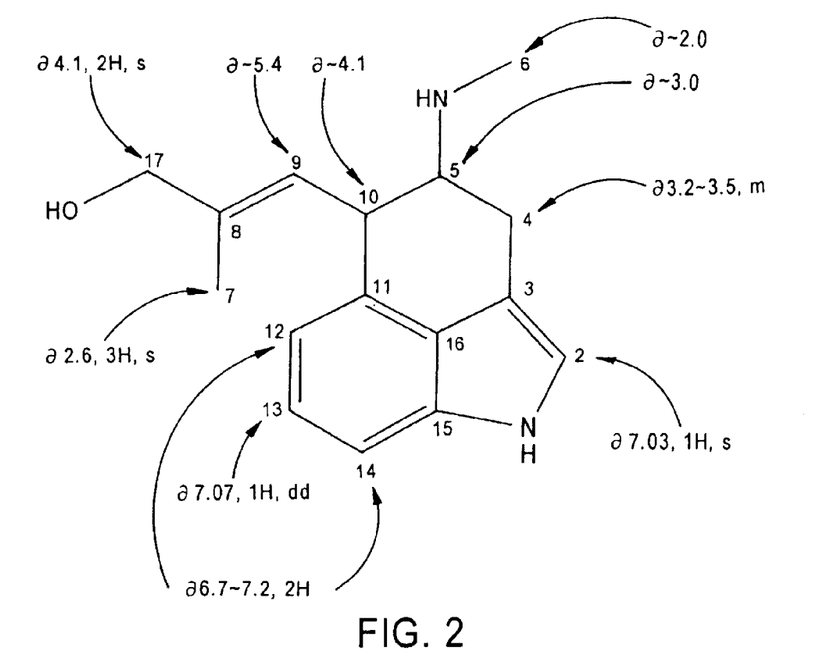
FIG. 2 is a structural view showing the chemical structure of chanoclavine.
Figure 3:
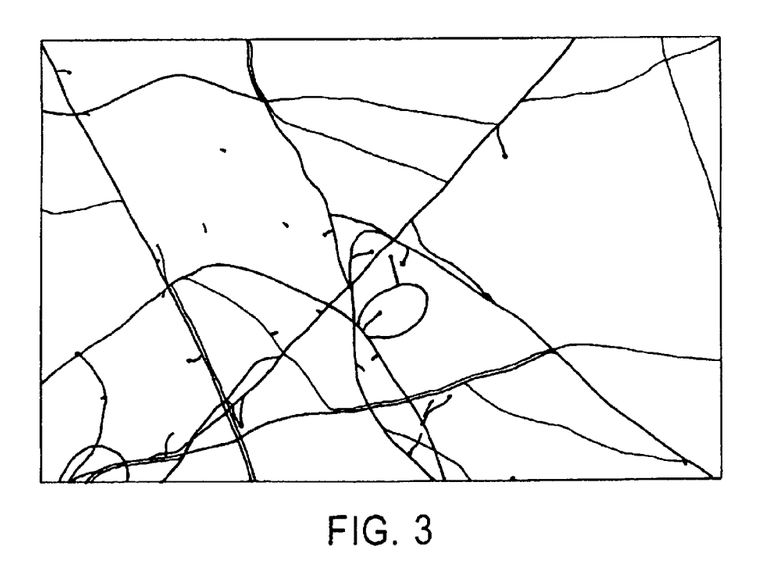
FIG. 3 is a photograph showing the morphology of a filamentous fungus.

As a result of FD-MS (Field Dissociated Ionization Molecular Weight Measurement), $M^+256$ was observed. Furthere in addition to fragment ions which gave a molecular peak at 256 in EI-MS, a fragmentation pattern specific to clavine alkaloids such as m/z 237 due to $-H3O+$ and m/z 155, 154 due to tricyclic stable ions was observed. When an examination was performed from the molecular formula suggested by EI-HR-MS, it was found that chanoclavine corresponded well with the molecular formula and the fragmentation pattern in EI. When NMR measurements were assigned as shown in FIG. 2, the isolated fragments were identified as chanoclavine. In the IR, absorptions were seen at 3400 (—OH), 1605 (C═C), 1420 and 1380 cm−1.

(9) Identification of Ergovaline

Here, it was examined whether or not the endophytes, which are symbiotic fungi living in endophyte-infected plants, produce ergovaline. The leaves and sheaths of freeze-dried plants infected with the endophytes were extracted by shaking for at least 30 minutes at room temperature with a mixed solution of 0.01N aqueous sodium hydroxide solution:chloroform=1:9. The extract was filtered on filter paper. Here, the filtrate was supplied to a silica gel column (Water Sep-Pak Plas Silica) conditioned with chloroform, and rinsed with chloroform. Fractions were eluted by a mixture of acetone:chloroform:acetic acid=80:20:0.05. The eluate was concentrated, dried and solidified, re-eluted with a 33% aqueous solution of methanol containing 0.1% ascorbic acid, and submitted for HPLC (High Performance Liquid Chromatography).

Figure 8:
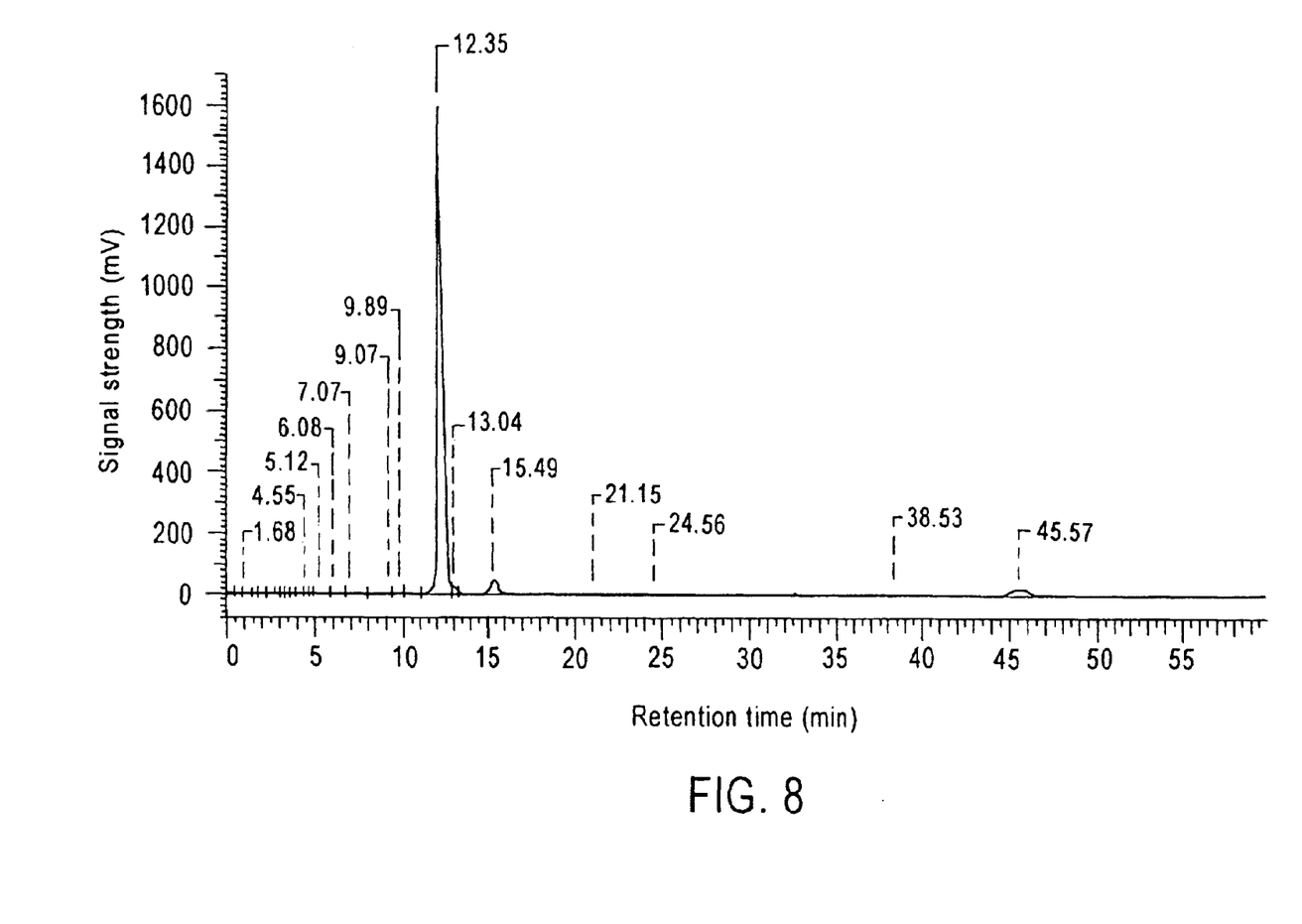
FIG. 8 is a graph showing the results of high performance liquid chromatography.

For the HPLC analysis, fluorescence detection was performed using a C18 column (3 um particle size, 4.6×7.5 mm), Ex (excitation wavelength) 310 nm and Em (fluorescence wavelength) 415 nm. When ergovaline tartrate, which is a sample of ergovaline, was analysed by HPLC, an ergovaline peak was observed in the vicinity of a retention time of 12 minutes as shown in FIG. 8. In other words, sample ergovalines showed a retention time peak at 12.35.

Figure 9:
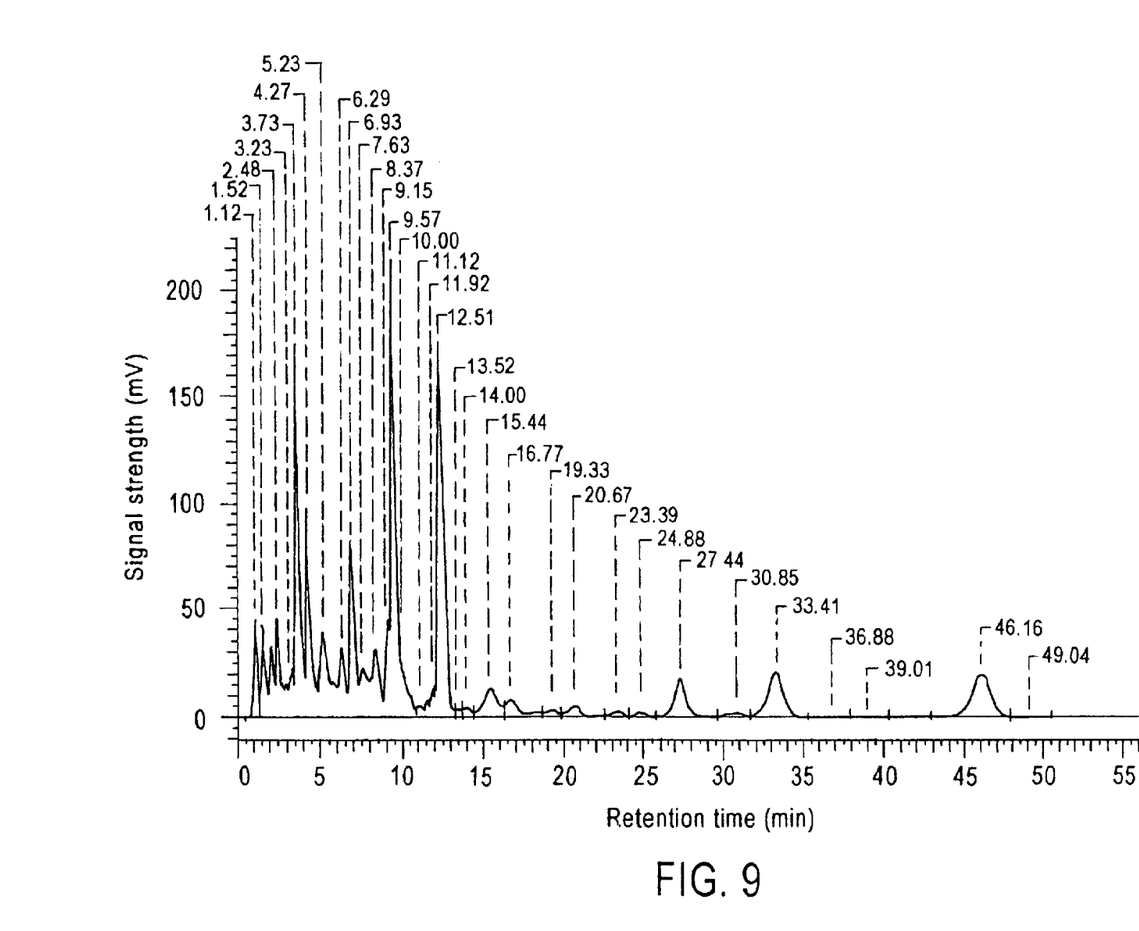
FIG. 9 is a graph showing the results of high performance liquid chromatography.

The presence or absence of ergovaline biosynthesis in endophyte-infected plants was determined by observing whether or not, in the case of the eluate obtained by the above method from endophyte-infected plants, there was a peak in the vicinity of a retention time of 12 minutes as for the samples in the HPLC analysis. As a result, for endophyte-infected plants other than those deposited at the Japanese National Institute of Bioscience and Human Technology, ergovaline was detected to the order of approximately 1 ppm (per dry weight) in the vicinity of a retention time of 12 minutes, as shown in FIG. 9. Specifically, for endophyte-infected plants other than those deposited at the Japanese National Institute of Bioscience and Human Technology, a peak was found near the same retention time as for the sample ergovaline, i.e., at 12.51, and this was confirmed to be due to ergovaline. The concentration was approximately 1 ppm per dry weight.

Figure 10:
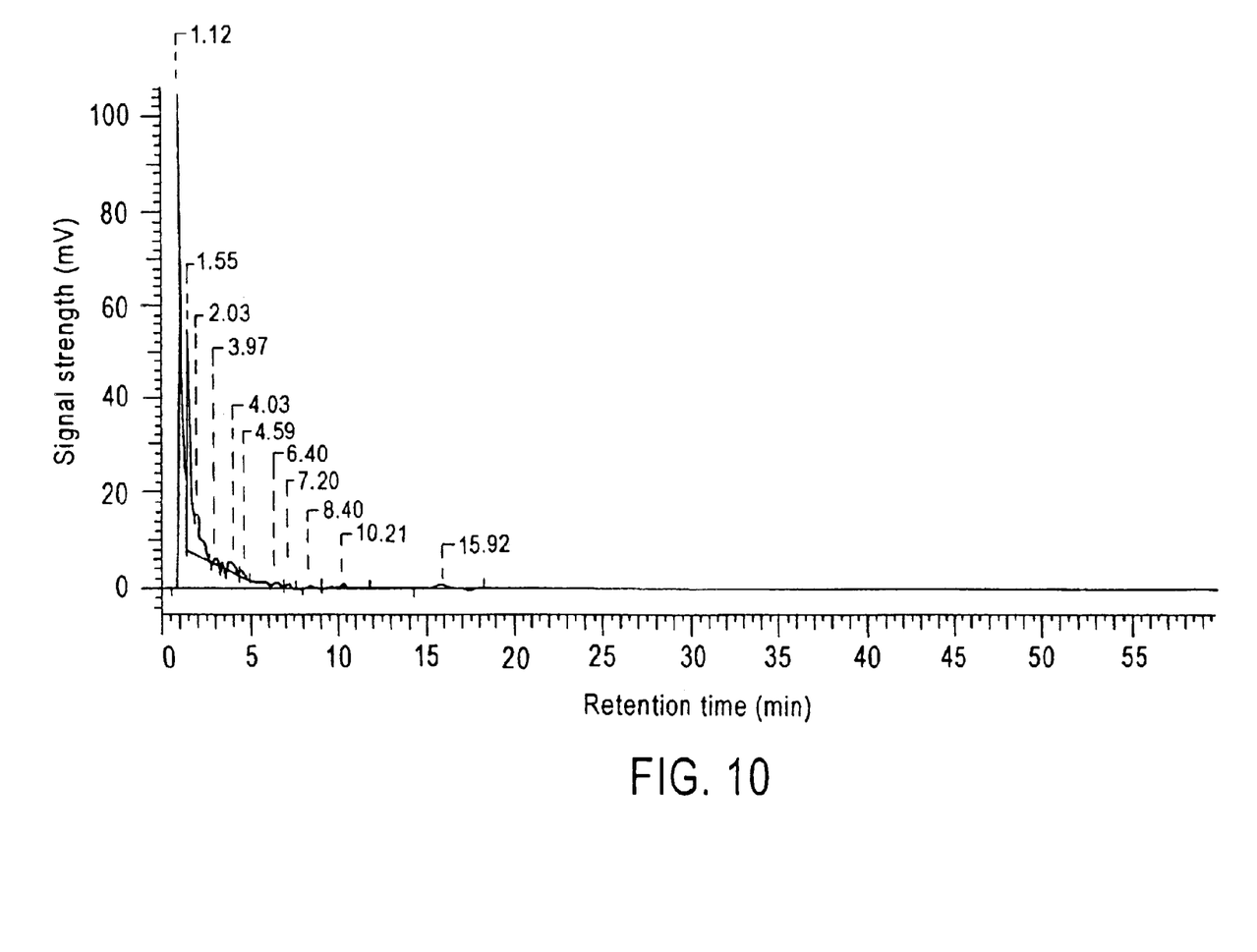
FIG. 10 is a graph showing the results of high performance liquid chromatography.

On the other hand, when HPLC analysis was performed by an identical method using plants infected with FERM P-17672 deposited at the Japanese National Institute of Bioscience and Human Technology, ergovaline was not detected, as shown in FIG. 10. Specifically, for plants infected with FERM P-17672 deposited at the Japanese National Institute of Bioscience and Human Technology, there were no peaks at all in the vicinity of a retention time of 12 min, confirming that ergovaline had not been produced. From the above results, it was clear that plants infected with FERM P-17672 do not biosynthesize ergovaline which is a toxic substance to livestock. Identical results were obtained for FERM P-17673, FERM P-17674.

(10) Comparative Test of Pest Resistance with other Fungi

A test of resistance to webworm which is a major pest in pasture grass was performed using plants belonging to the genus Poa infected with, for example, Neotyphodium sp. FERM P-17672 by the above method, and plants infected with fungus strains other than the above which were deposited at the Japanese National Institute of Bioscience and Human Technology.

Figure 11:
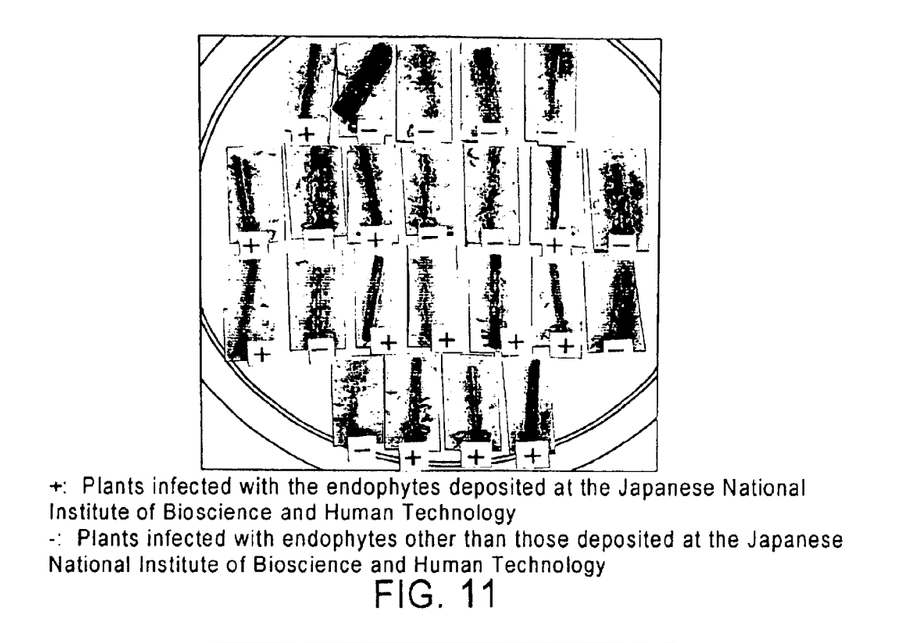
FIG. 11 is a photograph showing pest resistance tests.
Figure 12:
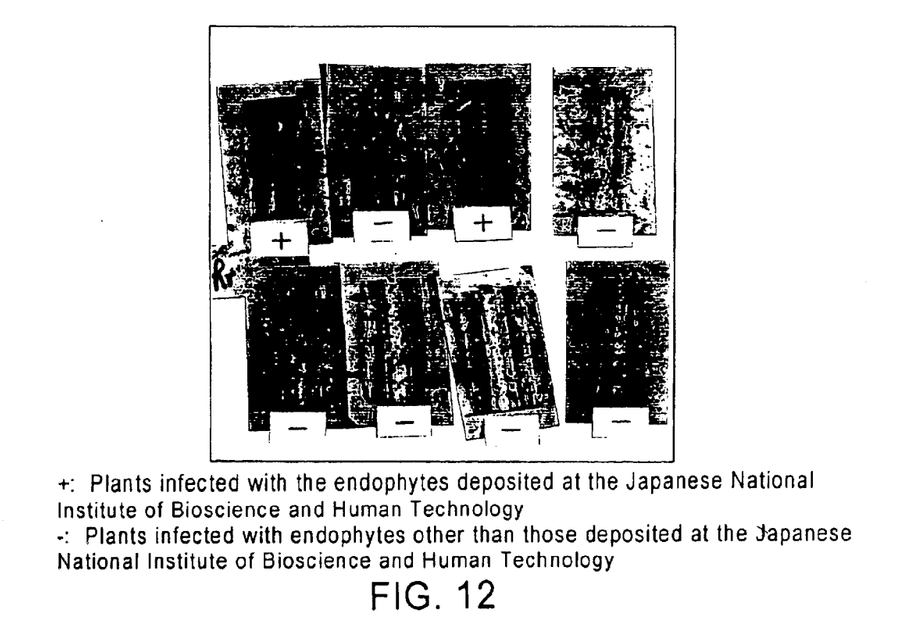
FIG. 12 is a photograph showing pest resistance tests.

Pest resistance tests were performed by releasing approximately 200 webworm larvae immediately after hatching in Petri dishes of diameter 9 cm containing respectively the above leaf sections, leaving in a room at 25° C., and examining the extent of damage after 24 hours and again after 48 hours. After 48 hours, whereas almost all the plants infected with fungi other than the fungi deposited at the Japanese National Institute of Bioscience and Human Technology had been consumed, the plants infected with Neotyphodium sp. FERN P-176723 had practically all their leaves remaining and showed strong resistance. The results obtained for Poa and Lolium are respectively shown in FIG. 11 and FIG. 12.

The test of resistance to webworm which is a major pest of pasture grass was performed in the same way as for plants of the genus Poa, for plants of the genus Lolium infected with FERM P-17672 by the above methods and fungus strains other than those deposited at the Japanese National Institute of Bioscience and Human Technology.

When the extent of the damage due to webworm was examined 24 hours after starting the test, it was found that, as in the case of plants belonging to the genus Poa, whereas plants infected with fungus strains other than those deposited at the Japanese National Institute of Bioscience and Human Technology had been practically consumed, plants infected with FERM P-17672 still had practically all their leaves, and showed strong resistance.

The results were identical when the other fungi deposited at the Japanese National Institute of Bioscience and Human Technology, FERM P-17673 and FERM P-17674, were used.

From the above results, it was confirmed that FERM P-17672, FERM P-17673 and FERM P-17674 deposited at the Japanese National Institute

Example 1

TABLE 1

Characteristics of fungus belonging to the genus Neotyphodium (FERM P-17672 deposited at the Japanese National Institute of Bioscience and Human Technology)

| Plant species | Infection of plant | Chanoclavine production in plant | Chanoclavine production on artificial culture | Seed propagation | Infection of plants raised from seed | Pest resistance to webworm |
|---|---|---|---|---|---|---|
| Agrostis | | | | | | |
| A. alba | +[1] | + | + | + | + | + |
| A. canina | + | + | + | + | + | + |
| A. palustris | + | + | + | + | + | + |
| A. tenuis | + | + | + | + | + | + |
| Festuca | | | | | | |
| F. arundinacea | + | + | + | + | + | + |
| F. ovina | + | + | + | + | + | + |
| F. o. var. duriuscula | + | + | + | + | + | + |
| F. pratensis | + | + | + | + | + | + |
| F. rubra | + | + | + | + | + | + |
| F. r. var commutata | | | | | | |
| Lolium | | | | | | |
| L. multiflorum | + | + | + | + | + | + |
| L. perenne | + | + | + | + | + | + |
| Poa | | | | | | |
| P. compressa | + | + | + | + | + | + |
| P. pratensis | + | + | + | + | + | + |
| P. trivialis | + | + | + | + | + | + |

[1] + signifies "yes"

of Bioscience and Human Technology confer strong pest resistance on the plants with which they are infected, as shown in Table 1.

Example 2

In this example, endophytes prior to infecting the plant were screened for by the screening method (7) of Embodiment 1, and endophytes which biosynthesized chanoclavine and which produced chanoclavine as the final metabolic product were selected. The symbiotic fungi screened for in this way were then used to infect the same plants as those of Embodiment 1 by the method of (4) of Embodiment 1, i.e., the grasses Agrostis, Festuca, Poa and Lolium. When screening was performed according to the method of (6) of Embodiment 1, it was confirmed that the plants were infected with symbiotic fungi producing chanoclavine as the final metabolic product. When pest resistance tests were performed on these plants according to the method of (10) of Embodiment 1, it was found that a substantially identical effect to that of Embodiment 1 was obtained.

Having described specific embodiments of this invention with reference to the accompanying drawings, it is to be understood that the invention is not limited to those precise embodiments or examples, and that various changes and modifications may be made by one skilled in the art without departing from the scope or spirit of the invention as described in the appended claims.

What is claimed is:

1. A composition comprising a biologically pure culture of a symbiotic filamentous fungus of the genus Neotyphodium, wherein the symbiotic fungus is a fungus selected from the group consisting of FERM BP-08480, FERM BP-08481 and FERM BP-08482 deposited at the Japanese National Institute of Bioscience and Human Technology, which produces one chanoclavine as the final metabolic product.

* * * * *